US008100849B2

(12) United States Patent
Movahed

(10) Patent No.: US 8,100,849 B2
(45) Date of Patent: Jan. 24, 2012

(54) METHOD AND APPARATUS TO REMOVE SUBSTANCES FROM VESSELS OF THE HEART AND OTHER PARTS OF THE BODY TO MINIMIZE OR AVOID RENAL OR OTHER HARM OR DYSFUNCTION

(75) Inventor: M. Reza Movahed, Newport Beach, CA (US)

(73) Assignee: Catharos Medical Systems, Inc., Campbell, CA (US)

( * ) Notice: Subject to any disclaimer, the term of this patent is extended or adjusted under 35 U.S.C. 154(b) by 291 days.

(21) Appl. No.: 11/894,328

(22) Filed: Aug. 20, 2007

(65) Prior Publication Data

US 2008/0021314 A1   Jan. 24, 2008

Related U.S. Application Data

(63) Continuation of application No. 10/057,202, filed on Jan. 23, 2002, now Pat. No. 7,363,072.

(60) Provisional application No. 60/263,865, filed on Jan. 23, 2001.

(51) Int. Cl.
*A61M 37/00* (2006.01)

(52) U.S. Cl. ............. 604/5.04; 604/4.01; 604/5.01; 604/96.01

(58) Field of Classification Search ........... 604/96.01, 604/4.01, 5.01, 5.04, 6.09, 6.11
See application file for complete search history.

(56) References Cited

U.S. PATENT DOCUMENTS

| | | | |
|---|---|---|---|
| 3,841,331 A | 10/1974 | Wilder et al. | |
| 4,689,041 A | 8/1987 | Corday et al. | |
| 4,927,412 A | 5/1990 | Menasche | |
| 5,324,260 A | 6/1994 | O'Neill et al. | |
| 5,411,479 A * | 5/1995 | Bodden | 604/101.03 |
| 5,568,809 A * | 10/1996 | Ben-haim | 600/433 |
| 5,597,377 A | 1/1997 | Aldea | |
| 5,653,690 A | 8/1997 | Booth et al. | |
| 5,695,457 A | 12/1997 | St. Goar et al. | |
| 5,814,016 A | 9/1998 | Valley et al. | |
| 5,916,193 A | 6/1999 | Stevens et al. | |
| 6,021,340 A | 2/2000 | Randolph et al. | |
| 6,537,495 B1 | 3/2003 | Cambron et al. | |
| 6,554,819 B2 * | 4/2003 | Reich | 604/508 |
| 6,699,231 B1 * | 3/2004 | Sterman et al. | 604/509 |
| 6,699,232 B2 | 3/2004 | Hart et al. | |
| 7,163,520 B2 * | 1/2007 | Bernard et al. | 604/6.09 |
| 2001/0052345 A1 * | 12/2001 | Niazi | 128/898 |
| 2004/0044302 A1 | 3/2004 | Bernard et al. | |

FOREIGN PATENT DOCUMENTS

| | | |
|---|---|---|
| WO | WO95/08364 A1 | 3/1995 |
| WO | WO96/32887 A1 | 10/1996 |
| WO | WO99/33407 A1 | 7/1999 |

* cited by examiner

*Primary Examiner* — Leslie Deak
(74) *Attorney, Agent, or Firm* — Bozicevic, Field & Francis LLP; Bret E. Field

(57) ABSTRACT

To accomplish isolation and removal of a substance from a vasculature, a catheter is employed to occlude a vessel of the vasculature. The substance is thus isolated in the vasculature and can be removed. In this way, the substance is removed before entering other parts of the circulatory system. This method is applicable to removal of contrast from the coronary sinus shortly after injection of the coronary arteries with the contrast. The method substantially minimizes or avoids renal dysfunction caused by angiographic procedures in which contrast must be injected. Such angiographic procedures are often performed during intervention procedures. This method substantially prevents circulation of the contrast to the kidneys where it could otherwise cause renal dysfunction or failure. The apparatus for implementation of the method is also disclosed.

2 Claims, 10 Drawing Sheets

_US 8,100,849 B2_

METHOD AND APPARATUS TO REMOVE SUBSTANCES FROM VESSELS OF THE HEART AND OTHER PARTS OF THE BODY TO MINIMIZE OR AVOID RENAL OR OTHER HARM OR DYSFUNCTION

RELATED APPLICATIONS

The present application is related to Disclosure Document serial number 480895, filed on Oct. 6, 2000, and is related to and claims priority under 35 USC 120 to U.S. Provisional Patent Applications 60/263,865 filed on Jan. 23, 2001, both of which are incorporated herein by reference.

BACKGROUND OF THE INVENTION

1. Field of the Invention

The invention relates to injecting a substance into a volume of the body and leaving the substance in the volume temporarily. The invention also relates to occluding the volume by a catheter and means for guiding the catheter to the volume. Such injection is of particular interest in the field of coronary angiography and coronary intervention, and particularly deals with the handling of the substance in the form of a contrast agent. The invention also relates to devices for the handling of contrast agent in the heart during angiographic and intervention procedures.

2. Description of the Prior Art

U.S. Pat. No. 6,021,340 to Randolph et al. has a guiding catheter for the coronary sinus. The guiding catheter of Randolph et al. has bent end portions as shown in FIGS. 8 to 11. This catheter has an occluding means in the form of a balloon 36. None of the bent portions are C-shaped or S-shaped as contemplated by the instant invention. Furthermore, the balloons 36 are disposed on straight portions of the catheter as shown n FIGS. 4 and 7.

An important difference between the device of Randolph et al. and the instant invention is that the bend in the end portion of Randolph's device is adapted for locating a device 70 in a branch 52 off the coronary sinus 50 for detecting electrical activity in the branch 52 off of the coronary sinus 50.

Randolph lacks providing any disclosure to injecting contrast by a second catheter upstream of the occlusion.

Randolph also lacks occluding for the purpose of isolating and removing contrast. The purpose of. Randolph's occlusion is to, "stop blood flow through the blood vessel in order to minimize misdirection of the contrast fluid and the dilution thereof which can interfere with fluoroscopic observation of the branch blood vessel."

US Patent Application Publication No. US 2001/0052345 to Niazi has a catheter to cannulate the coronary sinus. The device of Niazi has an inner catheter 12 and an outer catheter 10. Outer catheter 12 functions more like a guiding sheath, which is known and used in the art for guiding a catheter and which is inserted therein to be guided into a selected position. Therefore, the catheter combination of Niazi is different from the instant invention since it is not provided as a single catheter having a bent distal end for guiding the tip of the catheter.

The catheter pair of Niazi also varies from the instant invention in its purpose. Niazi has the purpose of locating and aiding in locating a pace lead, and the occlusion device 21 of Niazi is not intended for isolation and removal of contrast as is that of the instant invention.

Another difference between the catheter of Niazi and the instant invention is that the bend in the distal end of outer catheter is not particularly C-shaped. As best shown in FIGS. 2-5, the distal end portion appears to have a very particular configuration comprising angles and relative orientations in order to insert the pair of catheters into the coronary sinus via percutaneous insertion through the jugular or subclavian vein as can be understood by FIGS. 7 and 8.Niazi does not show or disclose engaging the coronary sinus with a catheter inserted via the femoral vein as is contemplated by the instant invention.

Furthermore, the device of Niazi does not have a second catheter inserted upstream of the veins for injecting contrast just before suctioning and removal of the contrast.

A related feature of the instant invention is that a volume of a vasculature may be viewed between the coronary arteries and the coronary sinus. This requires the second catheter of the instant invention.

Contrast usage during coronary angiogram or intervention in patients with renal disease is associated with substantial risk of renal failure in 30% of patients with renal disease and up to 50% in patients who have diabetes mellitus and renal failure. This side effect is responsible for long hospital stays and, in some patients, permanent renal damage requiring chronic dialysis. Any intervention that could decrease the amount of contrast exposure to the kidney would substantially decrease the risk of renal complications. It is well known that the amount of dye used in coronary intervention correlates with contrast induced nephropathy.

No procedure is known or currently used for removing contrast from a heart of a patient undergoing a diagnostic or an intervention procedure. Thus it is a primary object of the instant invention to provide a method and apparatus for removing contrast from a vessel of the heart during angiographic and intervention procedures on the heart.

The prevention of renal failure in patients undergoing coronary angiography or intervention by this method will substantially save lives and medical costs. As can be noted by the statistics set forth above, permitting contrast to enter a circulatory system of a patient with underlying renal disease is a major risk factor. The instant invention is a significant advance over the prior art in avoiding such high risk.

Furthermore, it is an object of the present invention to provide more generally a method and apparatus for temporarily injecting a substance into a volume or vessel of the human body for any of several purposes. The purposes include, but are not limited to: injection of therapeutic or medication fluids, diagnosis and/or research by injecting a contrast and imaging the interior of the volume or vessel, or for facilitating imaging of mechanical or chemical procedures in the interior of the volume or vessel.

It is a further object of the instant invention to provide a method and apparatus to accomplish the above objects, wherein the apparatus includes a controller to partially or completely automate the method.

BRIEF SUMMARY OF THE INVENTION

The instant invention is defined as a method and apparatus for removing a substance from a volume or vessel of the human body after it has been injected for therapeutic, diagnostic, or imaging purposes. It is contemplated that this invention is useful in many volumes, vessels, and organs of the body. However the illustrative embodiment is described in terms of the vessels of a heart for removing contrast from the vascular circulation.

The invention is also characterized as a method for minimizing renal failure due to contrast injected in a vascular system comprising the steps of disposing a catheter having a means for occluding in a selected portion of the vascular system. In the specific illustrative example relied upon most heavily in this disclosure, the vessel is a single vessel that may be occluded and the volume is the portion of the vessel and its branches upstream of the occlusion and downstream of the point of injection of the contrast. Thus, the volume more specifically describes the selected portion of the vascular system in terms of its interior and its capacity to hold blood and contrast. In the preferred embodiment the means for occluding is a balloon tip, and the preferred method of occluding is by inflating the balloon tip to selectively occlude the vascular system to thereby temporarily retain the contrast in the selected portion of the vascular system. At least a portion of the contrast is then removed from the vascular system while the contrast is temporarily retained in the selected portion of the vascular system until a predetermined concentration of the contrast in the vascular system is realized.

The apparatus comprises a catheter having an occlusion means to selectively occlude the vascular circulation to thereby temporarily retain the contrast in a selected portion of the vascular circulation. In the preferred embodiment, the occlusion means is a balloon on the catheter. A suction device selectively removes the contrast from the vascular circulation while it is temporarily retained in the selected portion of the vascular circulation. A controller stops the suction device when at least a predetermined amount of the contrast has been removed from the selected portion of the vascular circulation. The controller may be operated to provide repeated cycles of retaining the contrast in the selected portion, taking a series of angiographic images during each cycle, and then removing the contrast from the selected portion at the end of each cycle.

It is contemplated that other equivalent means for occluding may be employed. For example, an aspirating occlusion means may be employed wherein the apparatus is in the form of a catheter with an orifice through which a fluid is directed at a velocity and pressure to match the systemic flow at the occlusion point in the selected portion. Other equivalents might include mechanical or other expansion devices incorporated into any variety of means for occluding.

While the method and apparatus has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
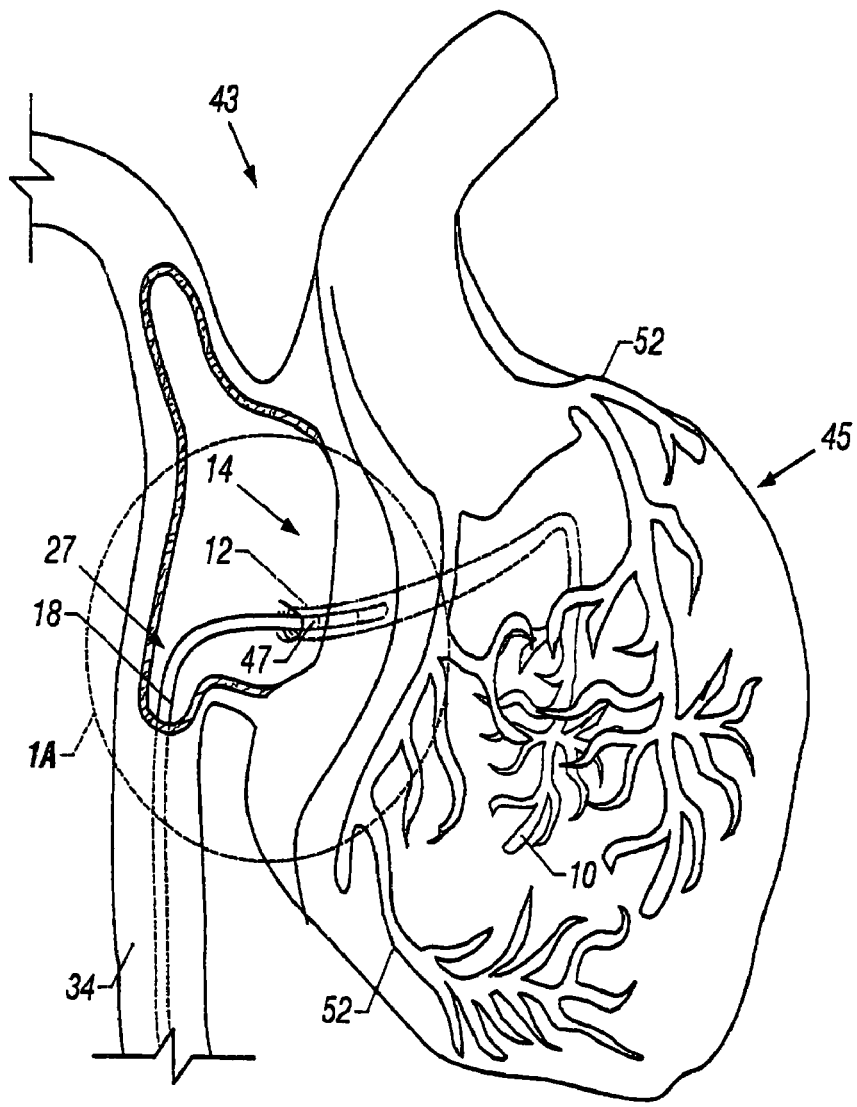
FIG. 1 is a diagrammatic front view of a heart and the step of inserting the first catheter therein.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Coronary veins 10 drain into the coronary sinus 12 as a final way of flow into the right atrium 14. Anatomically, it is possible to remove most of the contrast 16 from the coronary sinus 12 during coronary intervention by using a first catheter 18 that can occlude the coronary sinus vein 12 and remove blood 21 distal to the occlusion 23.

A balloon tipped catheter has been used safely for cardioplegia during cardiac surgery. However, a catheter having occlusion means as proposed by the present invention has never been used prior to the instant invention. One known manufacturer of balloon tipped catheters is Heartport Inc. of Redwood City, CA. The balloon tipped catheter by Heartport is manufactured for other applications. While the preferred means for occluding is a balloon tip 47, other means for occluding are possible, and the catheter of the instant invention has other features that go beyond what is disclosed in the prior art.

The apparatus of the instant invention is different from the prior art balloon tipped catheters. As such, the first catheter 18 of the instant invention is a modified catheter, and the apparatus comprises combination of the modified catheter 18 with other devices. The first balloon tipped catheter 18 can be inserted into the coronary sinus 12 very easily via a percutaneous access as is known in the art. The balloon tipped catheter 18 has a balloon 63 in the proximal end of the tip 47 that can occlude coronary sinus. The coronary sinus 12 is thus occluded distal to the balloon 63, so that blood 21 is stopped from proceeding downstream and can be collected easily with the first catheter 18 of the instant invention. The appropriate modifications to achieve the first catheter 18 are described below. It should be noted that any appropriately modified balloon tipped catheter may be employed in the invention and the Heartport catheter is mentioned only because it is an example of an accepted balloon tipped catheter for use in the coronary sinus 12.

Figure 3:
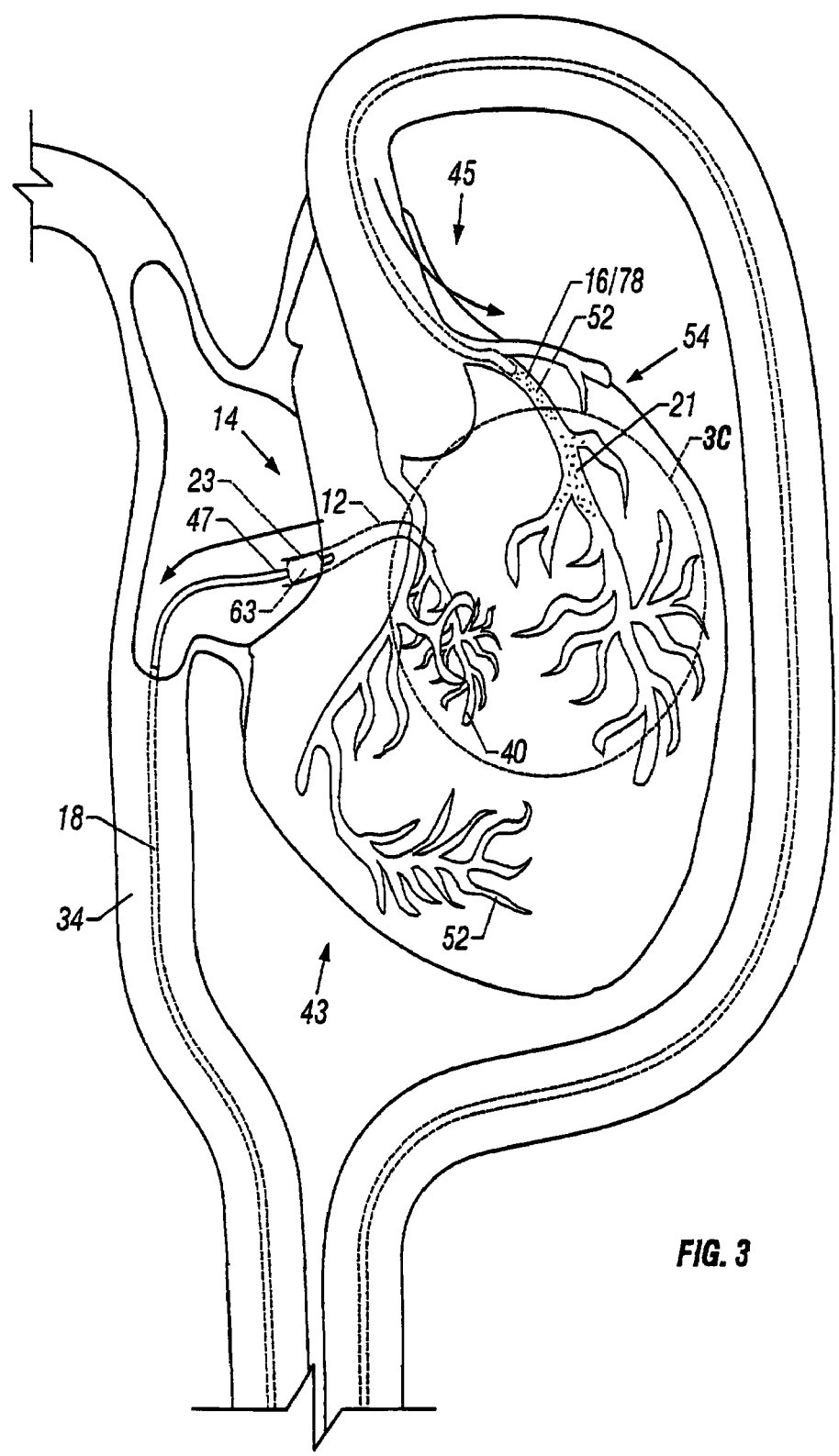
FIG. 3 is a diagrammatic front view of the heart with the step of inflating the balloon tip of the first catheter.

FIG. 1 is a diagrammatic front partial cross-sectional view of a first balloon tipped catheter 18 that has been modified according to the invention. The catheter 18 is modified so that it may be selectively inserted through the femoral vein 34 from the groin 36, or through the jugular or subclavian vein 38 through the neck 41 or chest 42 respectively. The modification is a rather sharp bend 27 at its distal end. The bend 27 can be C-shaped as shown at 30 or S-shaped as shown at 32 in FIG. 1A. The bend 27 may be preformed and permanent or it may be adjustable. The catheter 18 may be formed to permit adjustment while the catheter 18 is inserted in the body. As can be appreciated by the physical constraints of inserting the first catheter 18 into the coronary sinus 12, the tip 47 of the catheter 18 must follow a sinuous path to enter the heart 45 from the femoral vein 34 and then be inserted in the coronary sinus 12. These physical constraints and the need to navigate a sinuous path are best shown in FIG. 3.

Figure 1A:
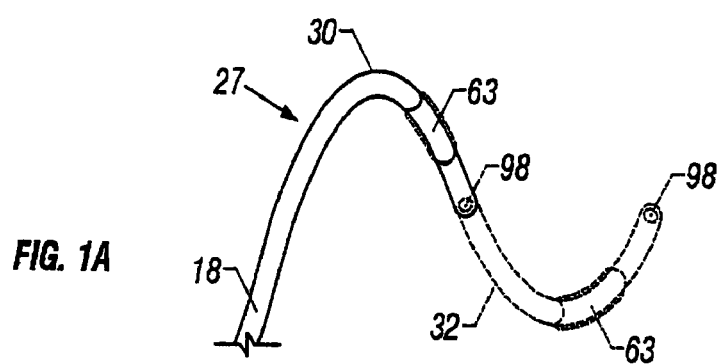
FIG. 1A is a detailed view of portion 1A of FIG. 1.

While FIG. 1A shows the distal end of the first catheter 18 in a generally C-shape or S-shape and the balloon 63 extending only along a small portion of the distal end, it is to be understood that the balloon may occupy any length of the catheter and thereby may assume a C-shape or an S-shape together with the catheter. These shapes are to be applied to the distal end or tip of the first catheter.

Safety would be a major issue for accessing the left side 54 of the heart 45 through the carotid. artery. That is why the second catheter 50 is inserted via the femoral artery from the groin 36. The second catheter 50 is normally used to inject contrast 16 in the coronary artery 52 on the left side 54 of the heart 45, which is upstream of the coronary sinus. Since the second catheter 50 must be inserted through the femoral artery in the groin 36, it is procedurally more practical to also access the right side 43 of the heart 45 by the first catheter 18 in the same area of the groin 36. In this way, a single attendant may monitor both percutaneous access points of the respective first and second catheters 18, 50 in the groin 36 area of the patient 56. However, access to the right side 43 of the heart 45 through the femoral vein 34 necessitates the modification of the balloon tipped catheter for the instant invention.

It should be noted that access to the right side 43 of the heart 45 is usually made through the jugular vein 38 in the neck 41. However, the catheter 18 of the instant invention selectively accesses the right side 43 of the heart 45 through the femoral vein 34 from the groin 36. Access through the femoral vein 34 provides the procedural advantage including greater convenience set forth above. Engaging the coronary sinus 12 with the catheter tip 47 is more difficult when the coronary sinus 12 is accessed through the femoral vein 34, as opposed to through the jugular vein 38. However, the procedural advantage that is achieved justifies the needed modifications for the instant invention. This is because access by a second catheter 50 is normally required in association with access by the first catheter 18 and access by the second catheter 50 is restricted to access from the groin 36 for safety reasons.

It should further be noted that guiding and positioning the catheters could be facilitated by conventional means including guide wires 58 and sheaths 61.

FIG. 1 shows the step of the method of using the instant invention that includes inserting the first catheter 18 into the coronary sinus.

Figure 2:
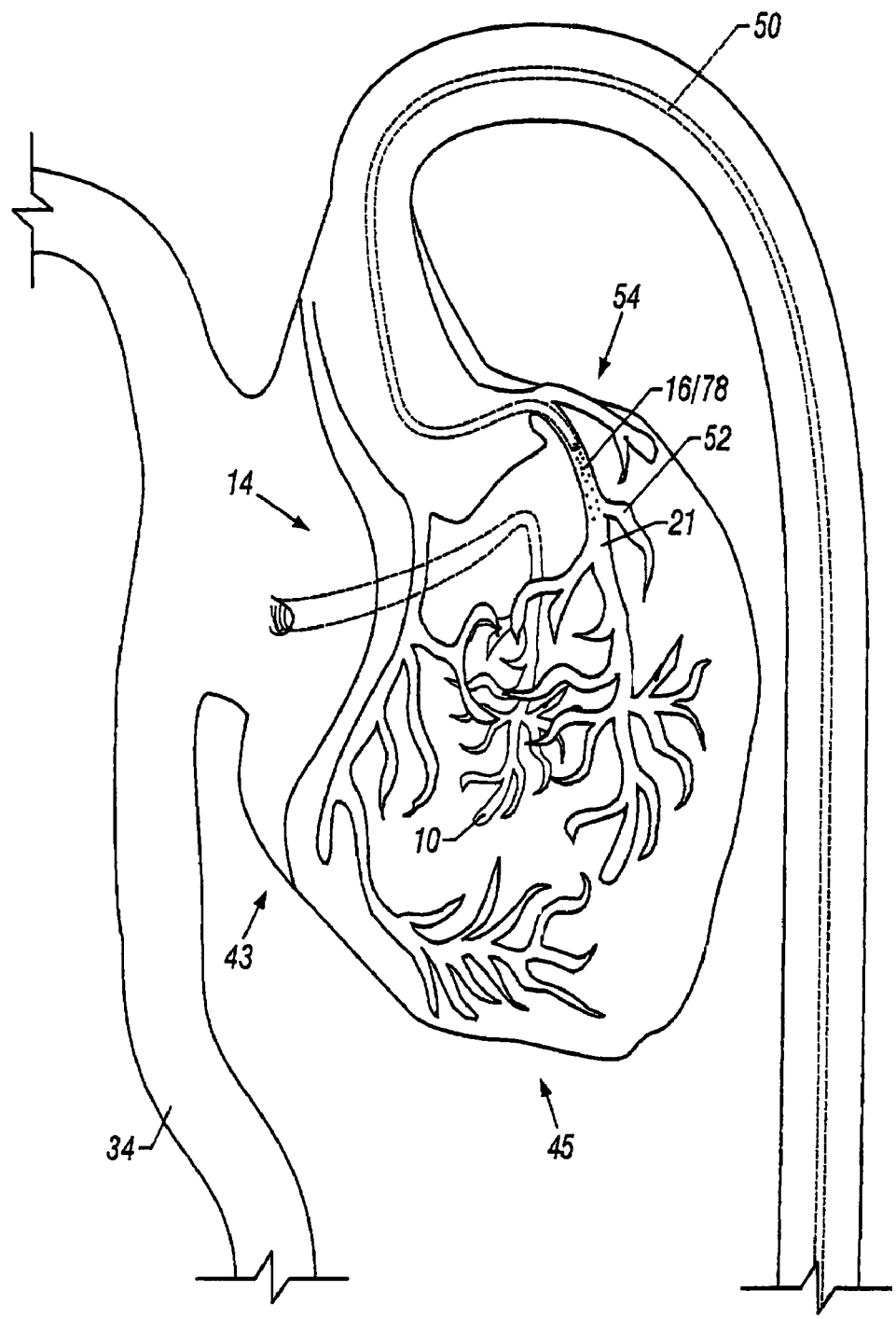
FIG. 2 is a diagrammatic front view of the heart and the step of inserting the second catheter therein.

FIG. 2 shows the step of the method including inserting the second catheter 50 into the coronary artery 52 via the femoral artery and injecting contrast.

FIG. 3 shows the step of occluding the coronary sinus with a balloon 63 of the balloon tip of the first catheter 18. This figure shows a large quantity of contrast 16 in the blood 21 distal to the occlusion 23. The inflation of the balloon 63 may be implemented from 15 minutes before injection of the contrast 16 to 3 seconds after injection of the contrast 16. However, the preferred time for inflation is approximately 1 second after injection of the contrast.

Figure 3A:
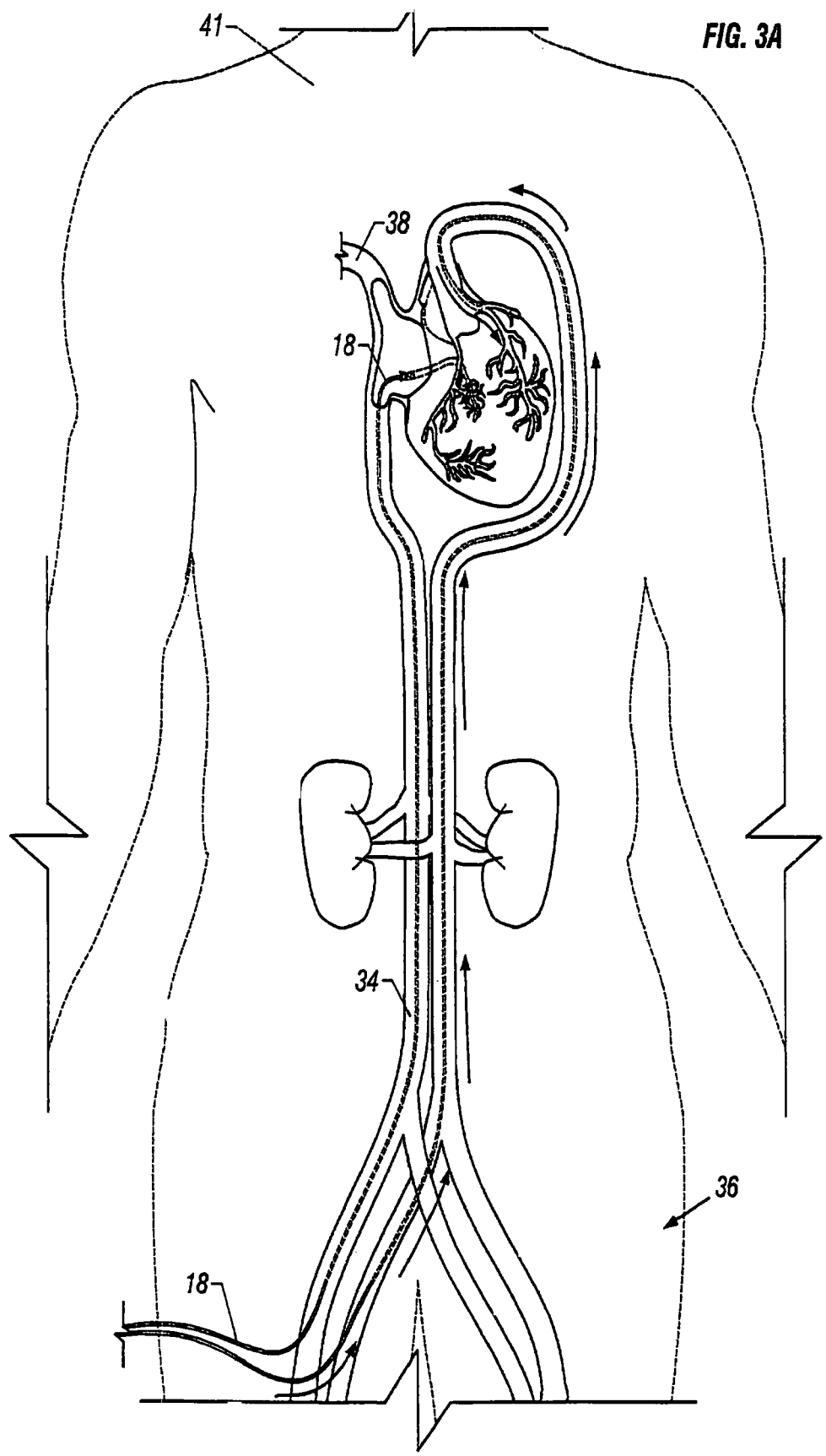
FIG. 3A is a diagrammatic front view showing the relationship of the major arteries and veins to the heart and with the first catheter inserted.

FIG. 3A provides a depiction showing the relationship of the major arteries and veins with respect to the heart 45. The relationships of the kidneys 67 and the groin 36 in the circulatory system are also shown. First catheter 18 is shown extending through the femoral vein 34.

Figure 3B:
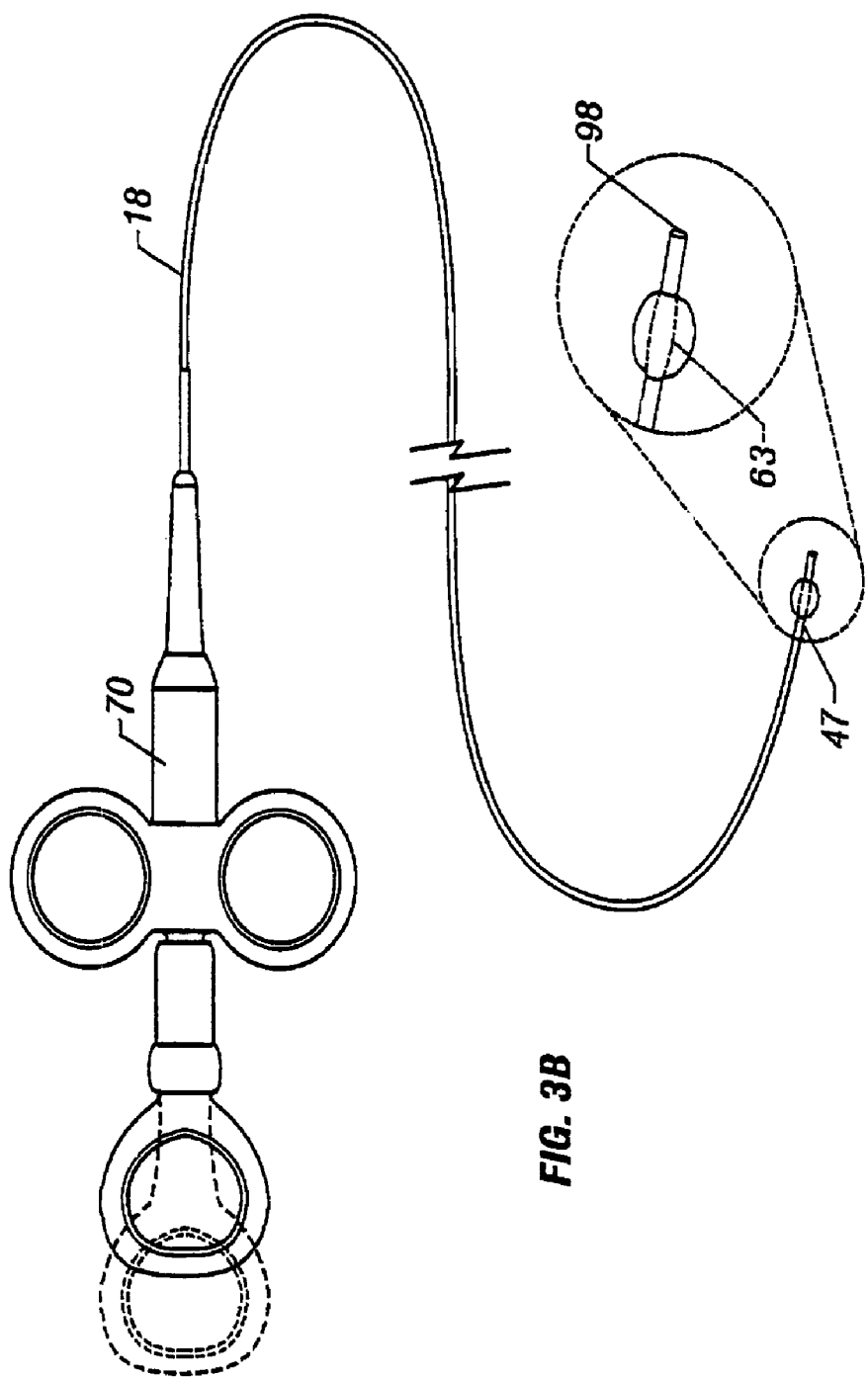
FIG. 3B is a diagrammatic side view of a syringe connected to the first catheter illustrating the balloon tip in the inflated and non-inflated positions.
Figure 3C:
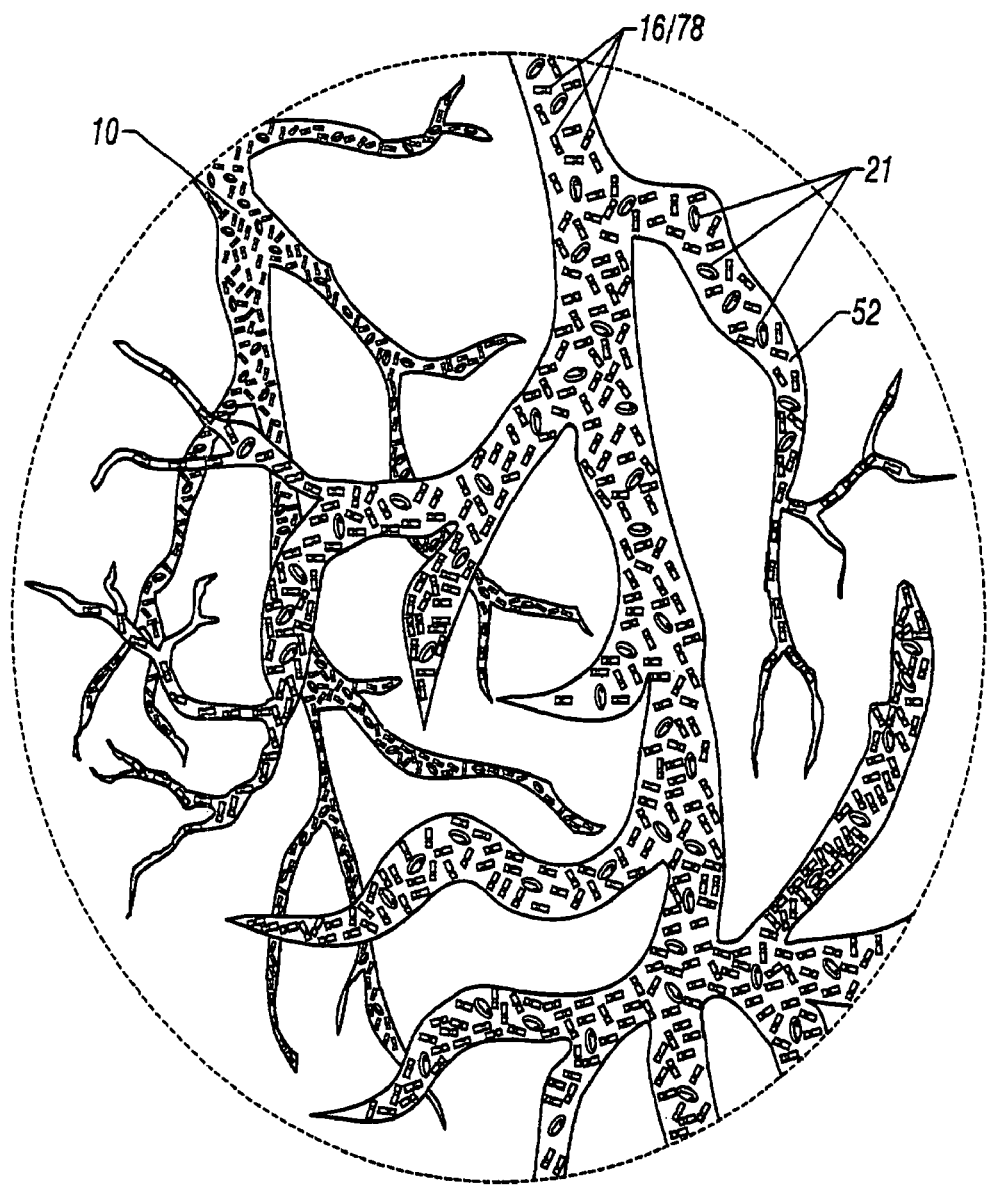
FIG. 3C is a detailed view of portion 3C of FIG. 3.

FIG. 3B illustrates a syringe 70 utilized for inflating and deflating the balloon 63. Syringes 70 may also be used to inject or remove contrast 16.

Figure 4:
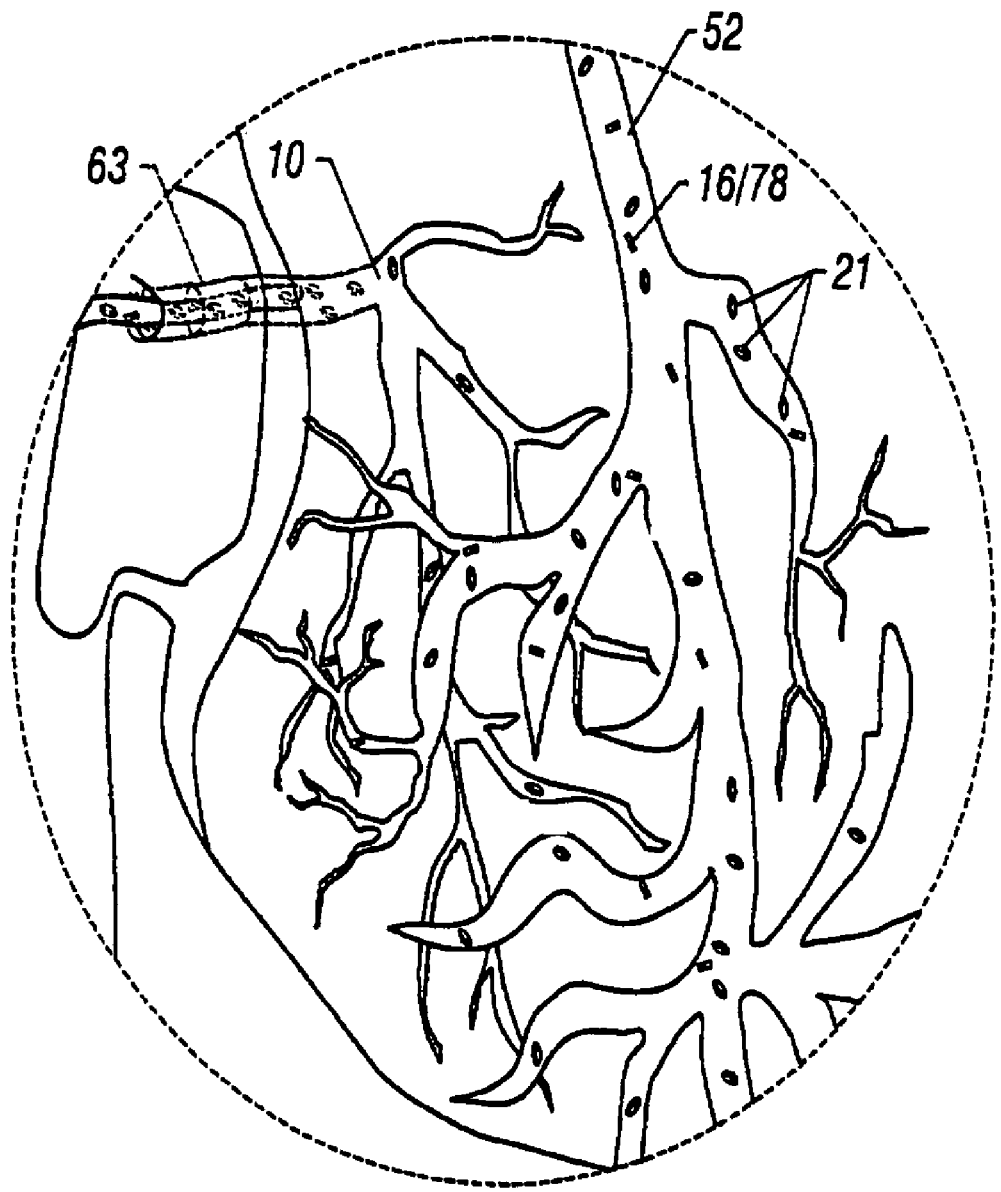
FIG. 4 is a front view similar to FIG. 3, showing the step of removal of blood 21 and contrast.

FIG. 4 illustrates the step of removing contrast 16 from the blood 21. As can be seen, there is less contrast 16 in FIG. 4 than there is in FIG. 3. This is due to suctioning through the first catheter 18 from a point distal to the balloon 63. The beginning of the suctioning should generally correspond with the inflation of the balloon 63. Normally the amount of blood 21 removed in several cycles of suctioning is not significant to endanger the patient 56 due to blood loss. However, suctioning for several minutes prior to injection is not recommended since it will contribute to significant blood loss. The preferred time to start the suctioning is 1 to 2 seconds after injection of the contrast The duration of suctioning may be from 3 to 20 seconds. However, preferably the duration of suctioning will be from 5 to 10 seconds.

Figure 4A:
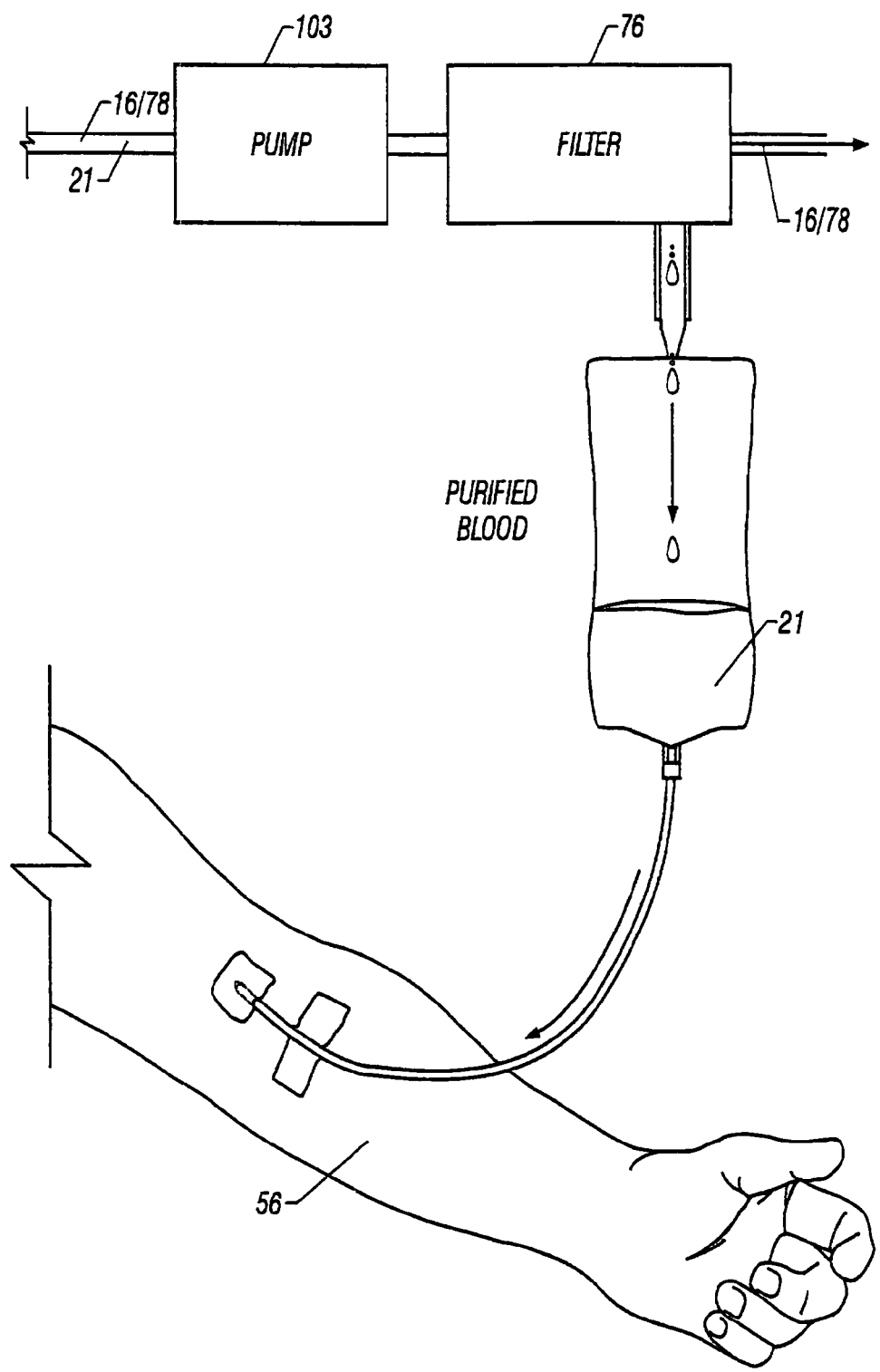
FIG. 4A is a diagrammatic view of a pump of the apparatus and a filter for removing contrast and returning purified blood to the patient.

FIG. 4A shows replacement of fluids by transfusion of the patient's own blood 21 that has been suctioned together with contrast, cleaned in a filter 76 to remove the contrast, and returned to the patient's body. Conventionally, an IV with saline solution or a blood 21 transfusion has been used to replace fluids lost during procedures. Replacement fluids may even be injected prior to a procedure in which blood loss is likely. However, the idea of recycling the patient's blood 21 by filtering and returning it to the patient's body has many advantages. Such filtering, in combination with the other aspects of the instant invention, has unique requirements due to the need to remove contrast 16 or some other substance 78 that may be used in a broader compass of the invention. In the arrangement of FIG. 4A, the purified blood would mainly comprise red blood cells. The remainder of the suctioned fluid would normally comprise blood plasma and the injected substance 78.

It is contemplated that filtering may be achieved by a membrane that catches everything but the red blood cells. Alternatively, centrifugation of the mixture of the contrast and the blood may be used in order to separate the red blood cells.

Indeed, an alternative means for removing contrast may be employed by suctioning blood and contrast at a sufficient rate from a vasculature to prevent a sufficient amount of contrast from proceeding downstream.

Figure 5:
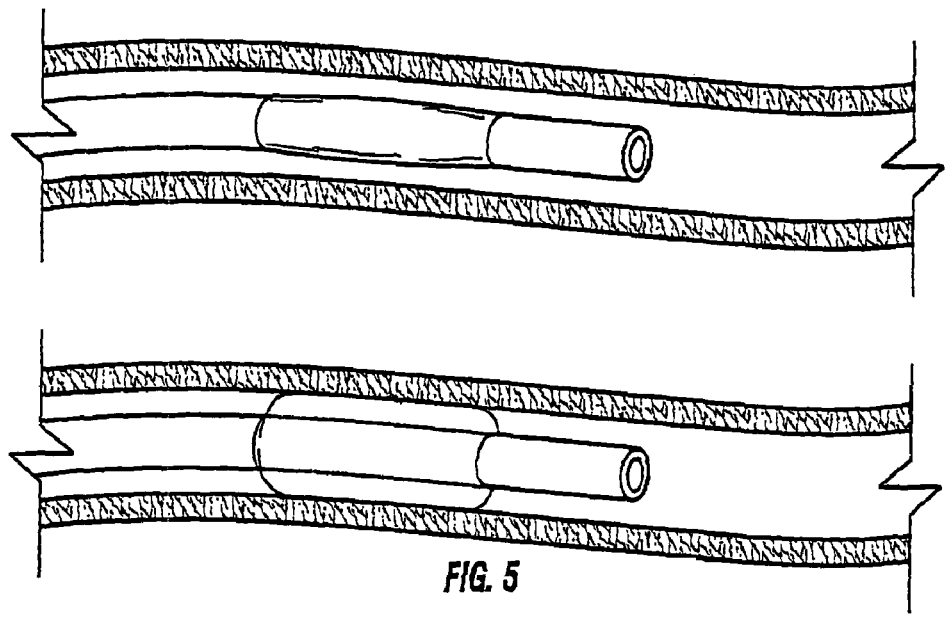
FIG. 5 is a partial section view of the catheter tip in a vessel with the balloon tip selectively deflated or left inflated.

FIG. 5 illustrates the step of selectively deflating the balloon 63 after the contrast 16 has been removed from the blood 21. As can be noted, the balloon 63 may be left inflated. This will not have an adverse affect on the heart 45 even if the balloon 63 were left inflated for several minutes. A possible side affect of leaving the balloon 63 inflated for long periods of time is that the coronary sinus may dilate slightly requiring further inflation to completely close off the coronary sinus vein 12.

The above description of steps in the method of the instant invention provides a general embodiment of the method of the instant invention. There are many other possible embodiments or variations of the method of using apparatus. Particularly, it is to be understood that the embodiments are described in terns of a specific procedure by way of example only. While the method is described with regard to a heart 45 and a specific volume and vessel of the heart 45, the method may be applicable in other volumes and/or vessels of the body where a substance 78 is to be temporarily injected and then removed.

A basic element of catheter 18 is a tip balloon 63. The balloon 63 may be of low profile in its deflated state so that catheter 18 can be inserted safely in to the coronary sinus, a main heart vein, or other vascular lumen or cavity.

In one embodiment of the invention, at least one sensor 81 is utilized to set off an alarm 83 or a signal 85 to alert an operator. Alternatively, the sensor 81 may be used to automatically actuate a subsequent step of the method. After injecting the heart arteries or coronary arteries with contrast, balloon 12, which is concurrently placed in a coronary vein 10, will be inflated. To accomplish this, at least one sensor 81 is utilized to set off an alarm 83 or signal 85 to alert an operator or to automatically actuate a subsequent step of the method. Thus, it can be seen that the sensor 81 may be incorporated in an active or a passive system. The passive system may be configured to also remove the upstream blood 21 that contains the contrast agent 16 from the vein 10 until a catheter tip sensor 81 detects low contrast 16 concentration and automatically deflates the balloon 63. In the active system, the sensor 81 selectively generates an alarm 83 or signal 85 to notify the operator to deflate balloon 63 when the contrast 16 concentration has reached a low level.

In another embodiment, at least one timer 90 is provided in a controller 92. In this embodiment, the timer 90 replaces the at least one sensor 81 to control deflation of the balloon 63. The timing of the deflation is measured from studies in humans that provide the appropriate time interval.

In this embodiment, the at least one timer 90 provides three predetermined times. A first predetermined time is the time of inflation of the balloon 63 relative to injection of the contrast. This time may be as early as 15 minutes before injection of the contrast 16 or as late as 3 seconds after the injection of the contrast. The late limit is determined at least in part by the size of the volume and/or vessel into which contrast 16 is being injected. Preferably, for the above described specific example, the occlusion should occur 1 second after the contrast 16 is injected. A second predetermined time is the time at which suctioning begins. As set forth above, the suctioning beginning time generally coincides with the occlusion start time. However, the timer 90 may alternatively start suctioning 1 to 2 seconds after contrast 16 is injected. A third predetermined time that can be controlled by the at least one timer 90 is the duration time of suctioning. The total duration of suctioning during a procedure may be important if such time corresponds to significant blood loss and potential danger or harm to the patient 56. However, under normal circumstances blood loss is not a concern and suctioning need not be limited to short intervals. Suctioning for a time in the range from 3 to 20 seconds should provide adequate short and long limits. However, suctioning duration is preferably in the range of 5 to 10 seconds for each cycle or for each time contrast 16 is injected.

Because of the ability to remove almost all of the contrast 16 used in the angiographic procedure without allowing it to circulate to the rest of the body, repeated cycles or pulses of contrast 16 may be employed with corresponding and synchronized occlusions and removals of the contrast 16. Not only does the invention allow the use of conventional angiographic techniques and contrast agents 16 with renally dysfunctional or sensitive patients, but it also allows for a new angiographic technique of pulsed angiography and new forms of contrast agents 16.

The method of the instant invention is not subject to the same stringent restrictions that were present before the invention. That is, restrictions based on the risk of harming a patient 56 by injecting too much contrast 16 have been substantially overcome. This is so because the contrast, which is harmful to the kidneys 67, is not permitted to enter the circulatory system of a patient 56 in any significant quantity when using the instant method. Thus, the method of the instant invention permits increased use of coronary angiography and intervention procedures in patients. This is especially true and beneficial for patients at high risk for contrast induced renal failure. With the instant method, many high risk patients that were previously ineligible for angiographic procedures will now become eligible.

The method of isolating and removing is not limited to use on human subjects. In fact, the method may be used on a mammalian or any living organism having a vascular system. However, the instant invention may particularly include isolating and removing at least a portion of a quantity of radiographic contrast medium that has been injected into the vasculature of a human or veterinary patient.

The method of this broadened compass of the invention may have several similar steps to those set forth in the specific example above. A primary step is inserting a first catheter having an occluder into a vessel to be occluded. Another step is inserting a second catheter to a location upstream of the occluder. Then contrast is injected into the patient's vasculature upstream of the occluder by the second catheter. An important step is to cause the occluder to occlude the vessel such that at least a portion of the injected contrast medium is retained upstream of the occluder. Then the contrast medium can be suctioned to remove the contrast medium from the vasculature that remains upstream of the occluder. Finally after the contrast medium has been removed, the occluder may be caused to cease occlusion of said vessel.

The method of the instant invention is not limited to the specific example of occlusion of a vessel in the heart, but may be applied at a variety of locations in the body. As such it is important to note that the orifice of the lumen for suctioning or for alternatively injecting a contrast or other substance may be located on the proximal side of the balloon. This is because the percutaneous insertion point may be upstream of an occlusion point in a region of a vasculature to be isolated. In this case, contrasts or other substances may be injected on the proximal side of the balloon as well.

Of course the occluder may be a balloon tip occluder having a balloon for occluding. Alternatively, the occluder may be of any type which functions to stop the flow of blood in a selected vessel of the vasculature. On the other hand, it should be understood that the details set forth specifically above apply equally in this broader compass of the instant invention. For example, the first, second, and third predetermined times may be applicable in veterinary and human patients.

The method in this broader compass of the invention may further include additional steps in conjunction with the sensors as set forth above. These steps include: providing a controller which communicates with the sensor; using the sensor to sense the presence of a predetermined quantity or concentration of a substance or physical characteristic; and sending a signal from the sensor to the controller when the sensor senses the predetermined quantity or concentration of said substance or physical characteristic.

Still further the method of the broader compass may include steps in conjunction with first and second conduits in the first catheter. In this aspect of the invention, the first conduit is connected to a first pump and the second conduit is connected to the second pump. The first conduit has a lumen or orifice at an end of said tip distal to said balloon and said second conduit is sealingly connected to the balloon. The first catheter is connected to a controller so that the controller actuates at least one device in the controller for coordinating other steps in said method when a signal is received in the controller.

The at least one other device may be an alarm, a switch, or a timer. The signal may be generated by manually actuating the controller when the presence of a sufficient amount of contrast is viewed radiographically upstream of the occluder.

Figure 6:
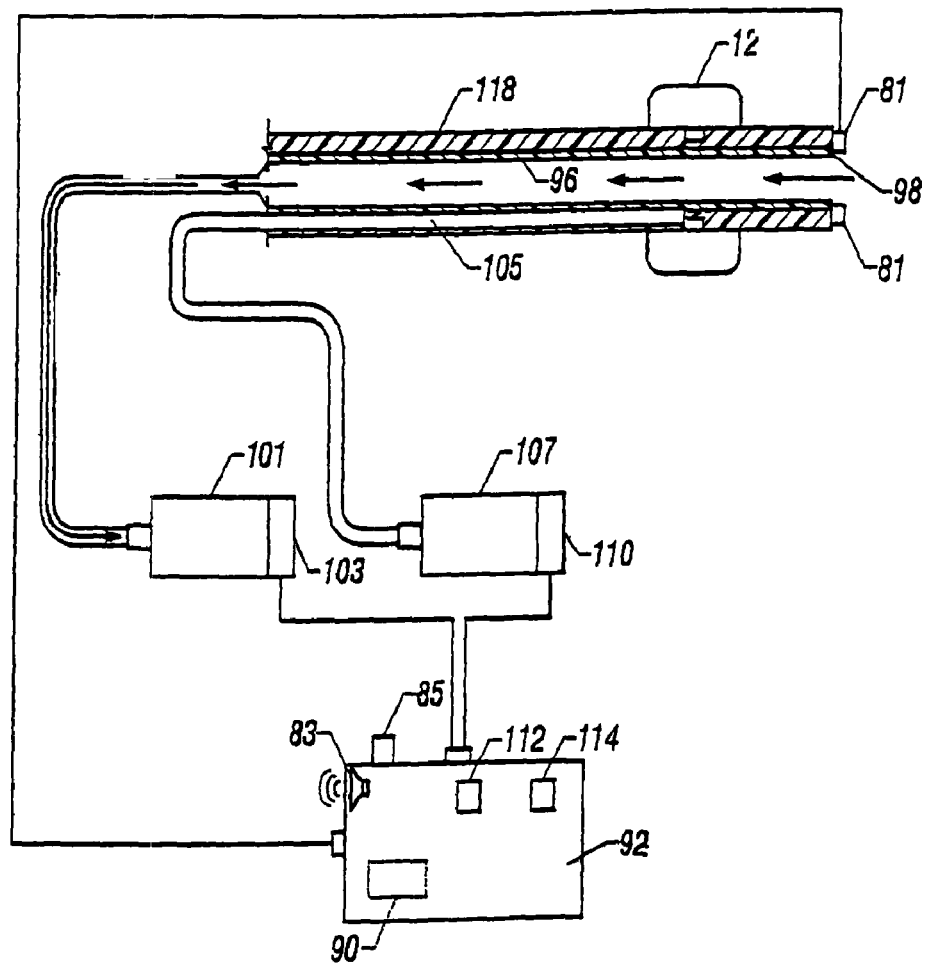
FIG. 6 is a simplified, diagrammatic, side cross-sectional view of a catheter system employed in the practice of the present invention.
Figure 7:
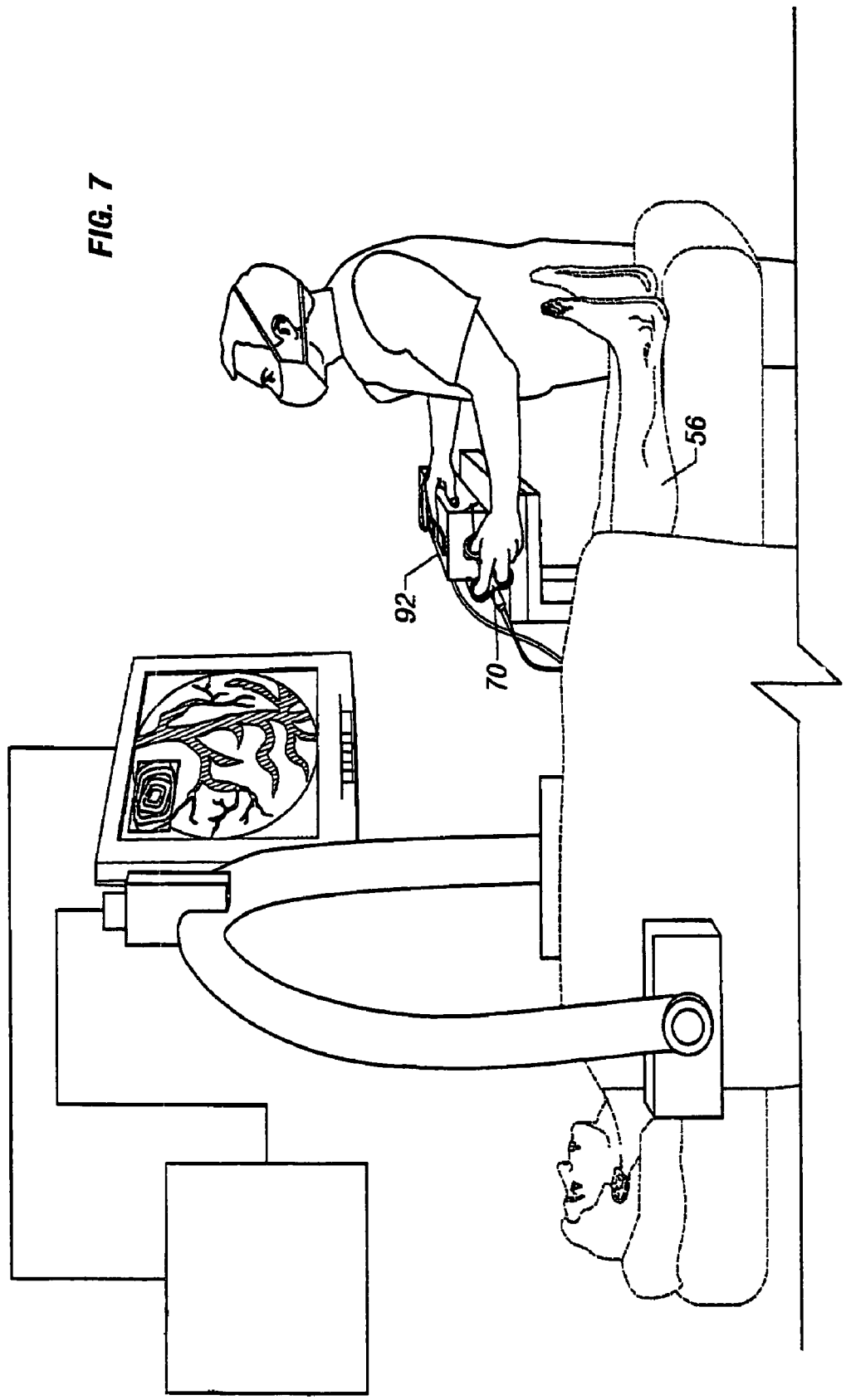
FIG. 7 is a perspective diagrammatic view of an operator implementing a method of the instant invention with the apparatus of the instant invention.

FIG. 6 is a diagrammatic side cross-sectional view of the balloon tipped catheter 18 of the apparatus of the instant invention. The apparatus is described below in terms of a specific procedure by way of example only. The apparatus may be used for other procedures in other parts of the body to provide similar advantages to those described in the illustrative specific examples of this disclosure.

One of the functions of catheter 18 is to remove dye or contrast 16 from coronary sinus 12 or other major heart vein 10 shortly after injecting the coronary arteries or heart arteries with contrast. To this end, first catheter 18 has a primary lumen 96 defined therein with a tip orifice 98 through which blood 21 can be suctioned out of the coronary sinus from tip 47. Suctioned blood 21 mixed with contrast agent 16 is collected in a collection bottle 101, which is maintained under a controlled partial vacuum by means of connection of a vacuum bottle or pump 103.

FIG. 6 further shows balloon 63, which communicates with a secondary lumen 105 defined in catheter 18. The secondary lumen 105 is proximally connected to a balloon 63 fluid reservoir 107. Fluid is used to inflate and deflate balloon 63 by means of a reversible pump 110 or other means communicated with reservoir 107.

Pumps 103 and 110 may be controlled manually, automatically or by a combination of manual and automatic steps. In a primarily manually controlled embodiment, at least first and second switch buttons 112, 114 on electronic controller 92 are selectively actuated to turn pumps 103, 110 on and off appropriately. Appropriate times for inflating and deflating the balloon 63 and for suctioning and stopping suctioning are determined in this case by observing the fluoroscopy screen to verify whether contrast 16 is present and its concentration in the volume and/or vessel. Switch button 114 has a switch with three positions to provide proper input to the reversible pump 110.

An alternative to the apparatus of FIG. 6 is achieved by replacing one or both pumps 103, 110 by a respective syringes 70. If both pumps 103, 110 are replaced, then the controller 92 and the switch buttons 112, 114 are also unnecessary. In this case the controller is the manual manipulation interface on the plungers of the syringes 70. The person operating the apparatus gives the input to this version of the controller by physical interface with the apparatus. Furthermore, in this version of the controller, a visual means in the form of the fluoroscopy screen provides indirect input to the apparatus via the operator and can thus be considered part of the controller.

A partially or fully automatic embodiment of the apparatus is achieved by means of electronic controller 92. In the case of partially automatic control, pumps 103 and 110 are appropriately activated by pressing switch buttons 112 and 114 on controller 92. The appropriate time to actuate the pumps 103, 110 may be indicated by a signal 85 or alarm 83 in the controller 92. The signal 85 or alarm 83 may be turned on by an input signal from at least one sensor 81 when the contrast 16 concentration levels have reached predetermined levels. In response to the signal 85 or alarm 83, an operator should press the appropriate switch button 112, 114. The signal or alarm 83 may be activated at upper levels to indicate the need to inflate the balloon 63 and begin suctioning. The signal 85 or alarm 83 may be activated at lower levels to indicate the need to stop suctioning and/or deflate the balloon 63. At that time, the operator turns suction pump 103 off and deflates balloon 63 by drawing fluid back into reservoir 107 by means of pump 110.

Alternatively, in a fully automated embodiment, controller 92 of the apparatus may automatically sense the signal 85 from sensor 81 and turn pumps 103, 110 on or off appropriately. Sensor 81 may be any type of sensor now known or later devised which may be able to return a signal which is directly or indirectly indicative of the presence of contrast agent 16 above or below a certain threshold or concentration. For example, a temperature sensor, a pH sensor, or a resistivity sensor may be employed to detect the temporary presence or absence of a substance 78 in the blood 21. The response of sensor 81 thus need not be specific to contrast agent 16, but to any injected substance in the blood 21.

In each of the alternatives from partially to fully automatic, the controller has internal switches actuated by the switch buttons 112, 114, by the at least one timer 90, or by the at least one sensor 81. These internal switches are not shown, but are conventional switches that can be used to turn pumps 103, 110, alarm 83, signal 85, timers 90, or other devices in the controller on and off.

The apparatus set forth above is really a system of apparati used together. As in the case of the method described above, this system may be described in terms of a broader compass of the invention. That is, as a system for removing a substance that has been injected into the vasculature of a human or veterinary patient.

The system of the broader compass of the invention includes a catheter having an expandable region. The expandable region is adapted to occlude a selected region of the vasculature when the expandable region is in an expanded state. In the broader compass, the occlusion of the selected region of the vasculature retains the substance in that region of the vasculature.

Similar to the previously described example, a suction device removes at least a substantial portion of the injected substance from the region of the vasculature. Furthermore, a control apparatus may be provided to stop said suction device when at least a predetermined amount of the injected substance has been suctioned from the region of the vasculature within which the substance has been retained.

As in the broadened compass of the method set forth above, the system is applicable in any living organism having a vascular system. However, of great interest is how the system of the instant invention may be applied to an anatomical vessel of a mammalian patient. All of the features of the specific examples above may be applied to the invention of broadened compass. For example, a controller may be similarly employed for starting and stopping the suction device at specific times.

The first catheter of the invention of the broadened compass may further comprise a lumen that extends through at least a portion of the catheter and has an aperture formed in the catheter upstream of the occluder similar to the specific examples set forth above. This feature enables the injected substance to be suctioned through the aperture and through the lumen.

Additionally, it should be noted that in the broader compass of the invention, that the instant method and apparatus may be used in organs other than the heart. That is, it is contemplated that the method and apparatus may be used in the brain, kidneys, lungs, or in any vasculature of the body.

In an experiment with the illustrated embodiment, a balloon tipped catheter was successfully used in one pig and blood 21 removed from the coronary sinus safely without any complications. The insertion of the catheter was performed under fluoroscopy without any difficulties. Complete occlusion of the coronary sinus was achieved as confirmed under fluoroscopy by injecting dye distal to the inflated balloon before the final phase. Pressure in the coronary sinus was measured and was mildly elevated before blood 21 removal. The analysis of the amount of removed contrast 16 or dye revealed that 67% of injected contrast 16 or dye was successfully removed from coronary sinus.

This preliminary demonstration suggests that the method is operable, practical and should be effective to protect kidneys 67 by removing the majority of contrast.

The concentration of the removed contrast 16 or dye in the collected blood 21 from the coronary sinus can be investigated by using well-established methods of chromatography of the collected blood sample, which are available commercially.

It will be possible to remove from 67 to 99 percent of contrast 16 with the procedure of the instant invention in humans. Furthermore, it is projected that 90 percent of the contrast 16 can be removed during procedures on humans in most cases. This is due to the fact that much of the contrast 16 that was not removed from the pig most likely escaped into the circulatory system of the pig through an additional vein, called the azygos vein since the azygos vein was not occluded during the experimental procedure. Humans do not have a coronary azygos vein, as do pigs. Therefore, occlusion of the coronary sinus vein 12 will provide complete isolation of the contrast 16 in the target volume in humans, and a very small remnant of contrast 16, if any, will escape into the circulatory system.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method of removing a substance from the coronary sinus in a body, said method comprising:
    inserting a distal end of a catheter into said coronary sinus;
    injecting a substance into a vessel location upstream of said coronary sinus; and
    suctioning blood and said substance with said catheter from said coronary sinus by manually actuating a controller when the presence of a sufficient amount of substance is viewed radiographically upstream of said distal end of said catheter.

2. The method according to claim 1, wherein said substance is a contrast agent.

* * * * *